United States Patent
Grubisic et al.

(10) Patent No.: US 11,906,518 B2
(45) Date of Patent: Feb. 20, 2024

(54) TUMOR CELL ANALYSIS USING APTAMERS AND MICROFLUIDIC SYSTEMS

(71) Applicant: X Development LLC, Mountain View, CA (US)

(72) Inventors: Ivan Grubisic, Oakland, CA (US); Ray Nagatani, San Francisco, CA (US)

(73) Assignee: X Development LLC, Mountain View, CA (US)

( * ) Notice: Subject to any disclaimer, the term of this patent is extended or adjusted under 35 U.S.C. 154(b) by 351 days.

(21) Appl. No.: 17/236,538

(22) Filed: Apr. 21, 2021

(65) Prior Publication Data

US 2022/0341934 A1    Oct. 27, 2022

(51) Int. Cl.

| | |
|---|---|
| *G01N 33/574* | (2006.01) |
| *G16B 5/20* | (2019.01) |
| *C12N 15/115* | (2010.01) |
| *C40B 30/04* | (2006.01) |
| *G16C 20/20* | (2019.01) |
| *G16C 20/50* | (2019.01) |
| *G16C 20/70* | (2019.01) |

(52) U.S. Cl.
CPC .......... *G01N 33/574* (2013.01); *C12N 15/115* (2013.01); *C40B 30/04* (2013.01); *G16B 5/20* (2019.02); *G16C 20/20* (2019.02); *G16C 20/50* (2019.02); *G16C 20/70* (2019.02); *C12N 2310/16* (2013.01); *C12N 2320/10* (2013.01); *G01N 2500/10* (2013.01)

(58) Field of Classification Search
CPC ............. G01N 33/574; G01N 2500/10; G01N 33/57492; G01N 2800/52; G01N 33/5308; C12N 15/115; C12N 2310/16; C12N 2320/10; C40B 30/04; G16B 5/20; G16B 35/10; G16B 40/20; G16C 20/20; G16C 20/50; G16C 20/70
See application file for complete search history.

(56) References Cited

U.S. PATENT DOCUMENTS

2021/0189385 A1    6/2021    Grubisic

OTHER PUBLICATIONS

Song, J., Zheng, Y., Huang, M., Wu, L., Wang, W., Zhu, Z., . . . & Yang, C. (2019). A sequential multidimensional analysis algorithm for aptamer identification based on structure analysis and machine learning. Analytical chemistry, 92(4), 3307-3314. (Year: 2019).*
Labib et al., *Aptamer and antisense-mediated two-dimensional isolation of specific cancer cell subpopulations*, J. Am. Chem. Soc., Feb. 9, 2016; DOI: 10.1021/jacs.5b10939, 7 pages.
Mamet et al., *De-novo discovery of tumoricidal aptamers in a DNA sequencing chip*, bioRxiv May 7, 2019; DOI: 10.1101/630830, 19 pages.
Vidic et al., *In silico selection approach to develop DNA aptamers for a stem-like cell subpopulation of non-small lung cancer adenocarcinoma cell line A549*, Radiol. Oncol. 52(2): Feb. 26, 2018, 8 pages.

* cited by examiner

*Primary Examiner* — Lori A. Clow
*Assistant Examiner* — Nidhi Dharithreesan
(74) *Attorney, Agent, or Firm* — Kilpatrick Townsend & Stockton LLP

(57) ABSTRACT

Methods described herein include receiving data from flowing a plurality of aptamers over a sample of tumor cells randomly affixed to a surface of a microfluidic device. The tumor cells may include one or more unknown tumor subtypes of cells. The plurality of aptamers may include a plurality of aptamer families. Each aptamer family of the plurality of aptamer families may be determined to bind to at least one possible subtype of the tumor cells. The data may include a measure of binding affinity of each aptamer family to the tumor cells. The method may include analyzing the measure of the binding affinity of each aptamer family to the tumor cells. The analyzing may include classifying the binding affinity. The method may also include determining one or more aptamer families that characterize the one or more unknown tumor subtypes of cells based on the classifying.

20 Claims, 6 Drawing Sheets

US 11,906,518 B2

TUMOR CELL ANALYSIS USING APTAMERS AND MICROFLUIDIC SYSTEMS

FIELD

The present disclosure relates to use of aptamers and microfluidic systems to analyze tumor cells. In particular, aptamer families may be used to characterize tumor subtypes of tumor cells and/or identify tumor subtypes of tumor cells.

BACKGROUND

Treating cancer or tumors is challenging because tumors are composed of complex populations of different cells with different mutations. As a result, chemotherapies may kill a subset of the population that is susceptible to the drug, but resistant subtypes within the population may eventually grow to replace the lost cells and dominate the population.

Sampling tumor cells to characterize the population is challenged due to the limited sample volume of tumor cells that are available via minimally invasive approaches (e.g., harvesting circulating tumor cells). Additionally, the time required to sequence the cells and characterize the tumor subtypes in the population (and develop an associated treatment plan) can be extensive, hampering the ability of physicians to react to and treat the tumor.

Using nucleic acid aptamers to bind protein receptors displayed on the surface of tumor cells enjoys the advantages of having high specificity, high sensitivity, and relatively low costs/high speed of manufacture (compared to monoclonal antibodies used in most diagnostic applications). Aptamers are also able to be sequenced quickly to determine the identity of the binding aptamer (and therefore the cell receptors that it binds, and the genetic identity of the tumor cell). However, aptamers have extremely low information content: as a result, it is very difficult to determine what an aptamer (or family of aptamers) has bound based on sequence information alone. There is a need to determine aptamers that bind to tumor cells to characterize the tumor cells and to identify tumor subtypes of tumor cells. These and other improvements are addressed in this disclosure.

BRIEF SUMMARY

In some embodiments, a method is provided that includes receiving data from flowing a plurality of aptamers over a sample of tumor cells randomly affixed to a surface of a microfluidic device. The tumor cells may include one or more unknown tumor subtypes of cells. The plurality of aptamers may include a plurality of aptamer families. Each aptamer family of the plurality of aptamer families may be determined by a prediction model to bind to at least one possible subtype of the tumor cells. The data may include a measure of binding affinity of each aptamer family to the tumor cells. The method may include analyzing the measure of the binding affinity of each aptamer family to the tumor cells. The analyzing may include classifying the binding affinity of each aptamer family to the tumor cells. The method may also include determining one or more aptamer families that characterize the one or more unknown tumor subtypes of cells based on the classifying.

In some embodiments, the measure of the binding affinity of each aptamer family is an elution time.

In some embodiments, the measure of the binding affinity each aptamer family is an amount of aptamers that bind to the tumor cells.

In some embodiments, the method includes identifying the one or more unknown subtypes of cells of the tumor cells to obtain one or more identified tumor subtypes based on: (i) the determining of the one or more aptamer families that characterize the one or more tumor subtypes of cells based on the classifying, and (ii) the at least one possible subtype of the tumor cells that each aptamer family is determined to bind to by the prediction model.

In some embodiments, the method includes determining a treatment protocol for a subject having the tumor cells based on the one or more identified tumor subtypes.

In some embodiments, the method includes treating the subject based on the treatment protocol.

In some embodiments, the sample is a liquid biopsy of the tumor cells obtained from a fluid of the subject.

In some embodiments, the method includes ascertaining a level of cancer based on the one or more identified tumor subtypes.

In some embodiments, the method includes treating a subject having the tumor cells using the one or more aptamer families that characterize the one or more tumor subtypes of cells.

In some embodiments, the plurality of aptamer families is at least 3 aptamer families.

In some embodiments, the plurality of aptamer families includes more aptamer families than a number of tumor subtypes of the one or more unknown subtypes of the tumor cells.

In some embodiments, the data includes results from flowing a first aptamer family and a second aptamer family concurrently over the tumor cells. The first aptamer family may be determined by the prediction model to bind to a first possible tumor subtype. The second aptamer family may be determined by the prediction model to bind to a second possible tumor subtype. The data may include results from flowing the first aptamer family and a third aptamer family concurrently over the tumor cells. The third aptamer family may be determined by the prediction model to bind to a third possible tumor subtype. The second aptamer family and the third aptamer family may not be flowed concurrently over the tumor cells. The method may further include determining that the measure of the binding affinity for the first aptamer family is greater than the measure of the binding affinity for the second aptamer family. The method may also include determining that the measure of the binding affinity for the third aptamer family is greater than the measure of the binding affinity for the first aptamer family. In addition, the method may include determining that the third possible tumor subtype has a higher population in the tumor cells than the first tumor subtype and that the first possible tumor subtype has a higher population than the second possible tumor subtype.

In some embodiments, a system may include one or more data processors. The system may further include a non-transitory computer readable storage medium containing instructions that, when executed on the one or more data processors, cause the one or more data processors to perform actions including receiving data from flowing a plurality of aptamers over a sample of tumor cells randomly affixed to a surface of a microfluidic device. The tumor cells may include one or more unknown tumor subtypes of cells. The plurality of aptamers may include a plurality of aptamer families. Each aptamer family of the plurality of aptamer families may be determined by a prediction model to bind to at least one possible tumor subtype of the tumor cells. The data may include a measure of binding affinity of each aptamer family to the tumor cells. The actions may further include analyzing the measure of the binding affinity of each aptamer family to the tumor cells. The analyzing may include classifying the binding affinity of each aptamer family to the tumor cells. The actions may also include determining one or more aptamer families that characterize the one or more unknown tumor subtypes of cells based on the classifying. The actions may include any method described herein.

In some embodiments, the actions further include identifying the one or more unknown subtypes of cells of the tumor cells to obtain one or more identified tumor subtypes based on: (i) the determining of the one or more aptamer families that characterize the one or more tumor subtypes of cells based on the classifying, and (ii) the at least one possible subtype of the tumor cells that each aptamer family is determined to bind to by the prediction model.

In some embodiments, the actions further include determining a treatment protocol for a subject having the tumor cells based on the identity of the one or more unknown tumor subtypes of cells.

In some embodiments, the actions further include ascertaining a level of cancer based on the identity of the one or more unknown tumor subtypes of cells.

In some embodiments, a computer-program product tangibly embodied in a non-transitory machine-readable storage medium, may include instructions configured to cause one or more data processors to perform actions including receiving data from flowing a plurality of aptamers over a sample of tumor cells randomly affixed to a surface of a microfluidic device. The tumor cells may include one or more unknown tumor subtypes of cells. The plurality of aptamers may include a plurality of aptamer families. Each aptamer family of the plurality of aptamer families may be determined by a prediction model to bind to at least one possible tumor subtype of the tumor cells. The data may include a measure of binding affinity of each aptamer family to the tumor cells. The actions may also include analyzing the measure of the binding affinity of each aptamer family to the tumor cells. The analyzing may include classifying the binding affinity of each aptamer family to the tumor cells. The actions may further include determining one or more aptamer families that characterize the one or more unknown tumor subtypes of cells based on the classifying. The actions may include any method described herein.

In some embodiments, the actions further may include identifying the one or more unknown subtypes of cells of the tumor cells to obtain one or more identified tumor subtypes based on: (i) the determining of the one or more aptamer families that characterize the one or more tumor subtypes of cells based on the classifying, and (ii) the at least one possible subtype of the tumor cells that each aptamer family is determined to bind to by the prediction model.

In some embodiments, the actions may further include determining a treatment protocol for a subject having the tumor cells based on the one or more identified tumor subtypes.

In some embodiments, the actions may further include ascertaining a level of cancer based on the one or more identified tumor subtypes.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

A better understanding of the nature and advantages of embodiments of the present invention may be gained with reference to the following detailed description and the accompanying drawings.

Figure 1A:
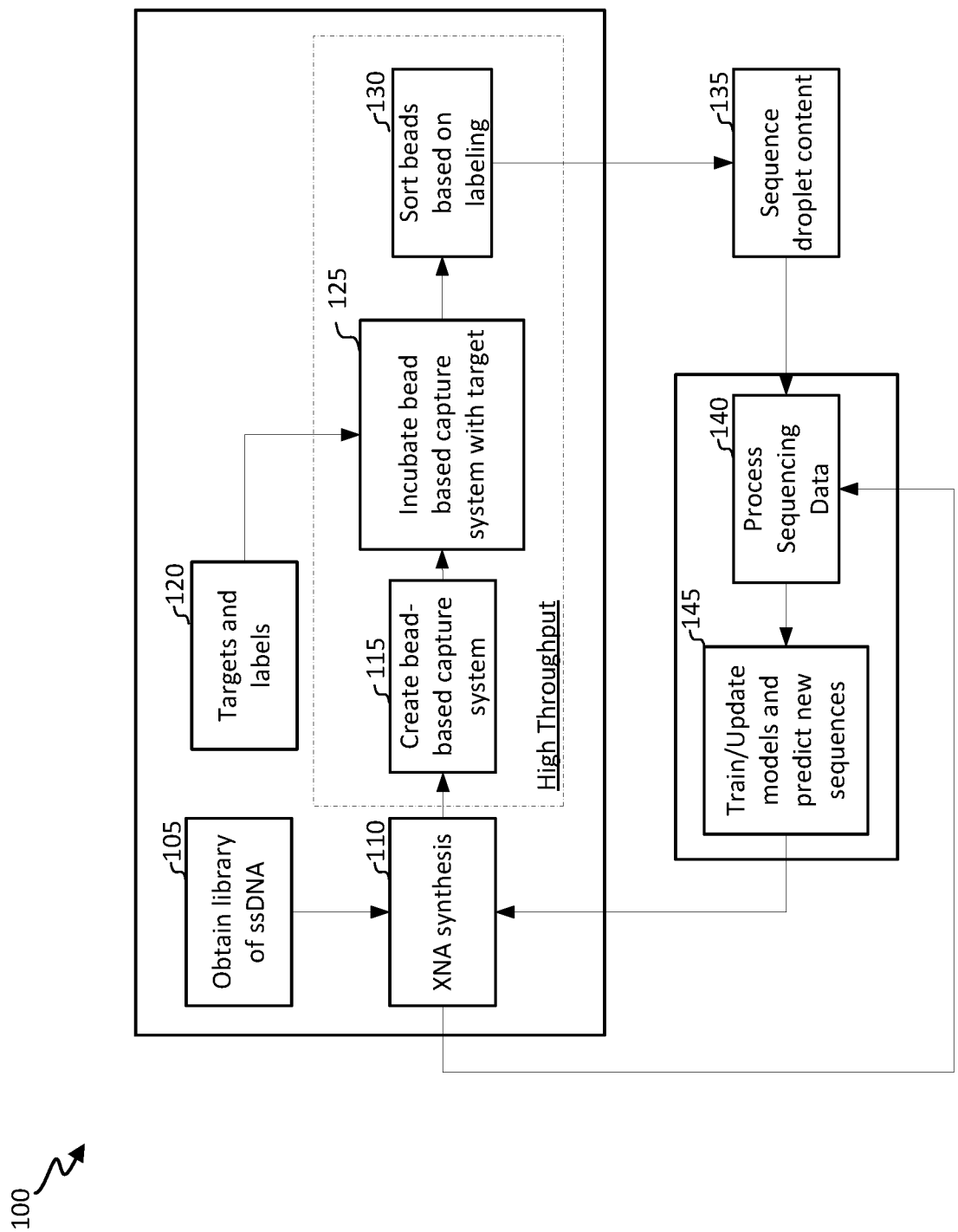
FIGS. 1A and 1B show block diagrams of an aptamer development platform according to various embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

I. Introduction

Aptamers may be used in treating tumors or cancer. Aptamers are short sequences of single-stranded oligonucleotides (e.g., anything that is characterized as a nucleic acid, including xenobases). The sugar backbone of the single-stranded oligonucleotides functions as the acid and the A (adenine), T (thymine), C (cytosine), G (guanine) refers to the base. An aptamer can involve modifications to either the acid or the base. Aptamers have been shown to selectively bind to specific targets (e.g., proteins, protein complexes, peptides, carbohydrates, inorganic molecules, organic molecules such as metabolites, cells, etc.) with high binding affinity. Further, aptamers can be highly specific, in that a given aptamer may exhibit high binding affinity for one target but low binding affinity for many other targets. Thus, aptamers can be used to (for example) bind to disease-signature targets to facilitate a diagnostic process, bind to a treatment target to effectively deliver a treatment (e.g., a therapeutic or a cytotoxic agent linked to the aptamer), bind to target molecules within a mixture to facilitate purification, bind to a target to neutralize its biological effects, etc. However, the utility of an aptamer hinges on a degree to which it effectively binds to a target.

Frequently, an iterative experimental process (e.g., Systematic Evolution of Ligands by EXponential Enrichment (SELEX)) is used to identify aptamers that are selectively bound to target molecules with high affinity. In the iterative experimental process, a nucleic acid library of oligonucleotide strands (aptamers) is incubated with a target molecule. Then, the target-bound oligonucleotide strands are separated from the unbound strands and amplified via polymerase chain reaction (PCR) to seed a new pool of oligonucleotide strands. This selection process is continued for a number (e.g., 6-15) rounds with increasingly stringent conditions, which ensure that the oligonucleotide strands obtained have the highest affinity to the target molecule. The nucleic acid library typically includes $10^{14}$-$10^{15}$ random oligonucleotide strands (aptamers). However, there are approximately a septillion ($10^{24}$) different aptamers that could be considered. Scalable machine-learning modeling techniques may be used to identify aptamers and derivatives thereof that selectively bind to target molecules with high affinity.

Tumor cells may include a plurality of subtypes, possibly resulting from mutations. Even if an aptamer or an aptamer family is known to bind to a specific monoclonal tumor cell, the tumor cells may include other subtypes that do not bind to the aptamer or aptamer family. As a result, information about the binding of a specific aptamer to a specific monoclonal tumor cell subtype may by itself not be useful in effectively treating a tumor or cancer.

Embodiments of the present invention identify aptamers that bind to a plurality of subtypes of tumor cells. Aptamers that bind to monocultures of common tumor subtypes may be identified. Sequence data of the aptamers that bind may be used to train machine learning models (e.g., Distributed Neural Network models) and design aptamer families predicted to preferentially bind the tumor subtype. The aptamer families are synthesized and may be labeled (e.g., with a colorimetric or fluorescent label).

A microfluidics flow cell is then used to determine binding between aptamer families and tumor subtypes. A tumor sample may be obtained by a minimally invasive procedure (e.g., liquid biopsy of circulating tumor cells). Tumor cells from the tumor sample are affixed to the surface of the flow cell. Probe reagents may be applied within the microfluidics flow cell. The reagents may be attached to aptamers to differentiate spectrophotometrically between aptamer families. Aptamers may be labeled prior to introduction to the sample. In some embodiments, aptamers may not be labeled. Unlabeled aptamers may be sequenced for detection, which avoids reagents for labeling and avoids certain detection equipment, thereby possibly saving time and cost. Sequencing rather than labeling for detection may also allow for determining differences in binding within an aptamer family. Aptamer families are flowed across the cells in various combinations. The combinations of aptamer families may be determined based on relative affinity for a particular tumor subtype (e.g., common or predominant tumor subtype) predicted by machine learning.

Machine learning predictions are performed prior to an in vitro experiment in a microfluidics flow cell. The machine learning may determine aptamer and aptamer families that may bind a particular tumor subtype or tumor subtypes. Certain common or predominant tumor subtypes may be known or suspected. These common or predominant tumor subtypes may be predicted to bind to certain aptamer families based on machine learning models. These predicted aptamer families may be used for the in vitro experiments.

Based on results from experiment(s) on the microfluidics flow cell, the binding affinity is assessed for the aptamer families. With the flow of aptamer families over tumor cells affixed to the flow cells, the aptamer families that bind the strongest to the tumor cells (including specific subtypes) will have the longest elution time. Aptamer elution time may be assessed downstream of the tumor sample (e.g., through an outlet port of the microfluidics flow cell). Elution time may be measured using a fluorescence or spectrophotometric detection system. The binding affinity or relative ranking of the binding affinity of each aptamer family may be used to estimate the relative population of each characterized tumor subtype and/or to indicate the optimal sequence of treatment via chemotherapy. In the event that no chemotherapy for the tumor subtype exists, the highest affinity and most specific aptamer family may be used to design an aptamer drug conjugate in which a non-specific cytotoxic agent can be affixed to biologically stable aptamers via a chemical linker/tether.

Embodiments described herein may be used in cancer diagnosis (to assess the ongoing changes in the tumor cell population), decision support (e.g., to identify the optimal chemotherapy to administer given changes in cell population), and/or treatment (e.g., via an aptamer drug conjugate strategy).

Using aptamers to characterize subtypes of tumor cells, to identify tumor subtypes, and/or to deliver treatments have advantages over existing methods for diagnosis and/or treatment. Aptamers have high sensitivity for material given their small size, enabling use in applications with target samples having small concentrations of tumor cells (e.g., liquid biopsies). In addition, aptamers are relatively cheap to make (compared to monoclonal antibodies) and are highly stable at room temperature, enabling probing with more diverse libraries (compared to antibodies). The search space for aptamer families that bind may be significantly reduced with machine learning prediction models. Aptamers may be characterized far more easily and faster than antibodies via next-generation sequencing.

Affixing tumor cells to the surface of the microfluidic flow cell and flowing aptamers over the tumor cells may more accurately replicate conditions for in vivo treating tumor cells with aptamers than if aptamers were affixed and tumor cells were flowed over the aptamers. Embodiments allow for a machine-learning enabled microfluidics approach to using aptamers for dynamic diagnosis and characterization of tumor cells.

II. Aptamer Development Techniques

FIG. 1A shows a block diagram of an aptamer development platform 100 for strategically identifying particular aptamers for in vitro experiments to assess queries such as binding affinities or product inhibition with respect to one or more particular targets. In various embodiments, the aptamer development platform 100 implements screening-based techniques for aptamer discovery where each aptamer candidate sequence in a library is assessed based on the query (e.g., binding affinity with one or more targets or functionally capable of inhibiting one or more targets) in a high-throughput manner. In some embodiments, the aptamer development platform 100 implements machine learning based techniques for enhanced aptamer discovery where each aptamer candidate sequence in a library that satisfies the query is input into one or more machine-learning models to predict additional aptamer candidate sequences that potentially satisfy the query. In some embodiments, the aptamer development platform 100 further implements screening-based techniques for aptamer validation to validate or confirm that the predicted additional aptamer candidate sequences do satisfy the query (e.g., bind or inhibit the one or more targets). As should be understood, these techniques from screening through prediction to validation can be repeated in one or more closed loop processes sequentially or in parallel to ultimately assess any number of queries in a high through-put manner.

The aptamer development platform 100 includes obtaining one or more single stranded DNA (deoxyribonucleic acid) or RNA (ribonucleic acid) (ssDNA [single-stranded DNA] or ssRNA [single-stranded RNA]) libraries at block 105. The one or more sssDNA or ssRNA libraries may be obtained from a third party (e.g., an outside vendor) or may be synthesized in-house, and each of the one or more libraries typically contains up to $10^{17}$ different unique sequences. At block 110, the ssDNA or ssRNA of the one or more libraries are transcribed to synthesize a Xeno nucleic acid (XNA) aptamer library. XNA aptamer sequences (e.g., threose nucleic acids [TNA], 1,5-anhydrohexitol nucleic acid [HNA], cyclohexene nucleic acid [CeNA], glycol nucleic acid [GNA], locked nucleic acid [LNA], peptide nucleic acid [PNA], FANA [fluoro arabino nucleic acid]) are synthetic nucleic acid analogues that have a different sugar backbone than the natural nucleic acids DNA and RNA. XNA may be selected for the aptamer sequences as these polymers are not readily recognized and degraded by nucleases, and thus are well-suited for in vivo applications. XNA aptamer sequences may be synthesized in vitro through enzymatic or chemical synthesis. For example, an XNA library of aptamers may be generated by primer extension of some or all of the oligonucleotide strands in a ssDNA library, flanking the aptamer sequences with fixed primer annealing sites for enzymatic amplification, and subsequent PCR amplification to create an XNA aptamer library that includes $10^{12}$-$10^{17}$ aptamer sequences.

In some instances, the XNA aptamer library may be processed for application in downstream machine-learning processes. In certain instances, the aptamer sequences are processed for use as training data, test data, or validation data in one or more machine-learning models. In other instances, the aptamer sequences are processed for use as actual experimental data in one or more trained machine-learning models. In either instance, the aptamer sequences may be processed to generate initial sequence data comprising a representation of the sequence of each aptamer and optionally a count metric. The representation of the sequence can include one-hot encoding of each nucleotide in the sequence that maintains information about the order of the nucleotides in the aptamer. The representation of the sequence can additionally or alternatively include a string of category identifiers, with each category representing a particular nucleotide. The count metric can include a count of each aptamer in the XNA aptamer library.

At block 115, the aptamers within the XNA aptamer library are partitioned into monoclonal compartments (e.g., monoclonal beads or compartmentalized droplets) for high-throughput aptamer selection. For example, the aptamers may be attached to beads to generate a bead-based capture system for a target. Each bead may be attached to a unique aptamer sequence generating a library of monoclonal beads. The library of monoclonal beads may be generated by sequence-specific partitioning and covalent attachment of the sequences to the beads, which may be polystyrene or glass beads. In some instances, the sequence-specific partitioning includes hybridization of XNA aptamers with capture oligonucleotides having an amine modified nucleotide for interaction with covalent attachment chemistries coated on the surface of a bead. In certain instances, the covalent attachment chemistries include N-hydroxysuccinimide (NHS) modified PEG, cyanuric chloride, isothiocyanate, nitrophenyl chloroformate, hydrazine, or any combination thereof.

At block 120, a target (e.g., proteins, protein complexes, peptides, carbohydrates, inorganic molecules, cells, etc.) is obtained. The target may be obtained as a result of query posed by a user (e.g., a client or customer). For example, a user may pose a query concerning identification of ten aptamers with the highest binding affinity for a given target or twenty aptamers with the greatest ability to inhibit activity of a given target. In some instances, the target is tagged with a label such as a fluorescent probe. At block 125, the bead-based capture system is incubated with the labeled target to allow for the aptamers to bind with the target and form aptamer-target complexes.

At block 130, the beads having aptamer-target complexes are separated from the beads having non-binding aptamers using a separation protocol. In some instances, the separation protocol includes a fluorescence-activated cell sorting system (FACS) to separate the beads having the aptamer-target complexes from the beads having non-binding aptamers. For example, a suspension of the bead-based capture system may be entrained in the center of a narrow, rapidly flowing stream of liquid. The flow may be arranged so that there is separation between beads relative to their diameter. A vibrating mechanism causes the stream of beads to break into individual droplets (e.g., one bead per droplet). Before the stream breaks into droplets, the flow passes through a fluorescence measuring station where the fluorescent label which is part of the aptamer-target complexes is measured. An electrical charging ring may be placed at a point where the stream breaks into droplets. A charge may be placed on the ring based on the prior fluorescence measurement, and the opposite charge is trapped on the droplet as it breaks from the stream. The charged droplets may then fall through an electrostatic deflection system that diverts droplets into containers based upon their charge (e.g., droplets having beads with aptamer-target complexes go into one container and droplets having beads with non-binding aptamers go into a different container). In some instances, the charge is applied directly to the stream, and the droplet breaking off retains a charge of the same sign as the stream. The stream may then returned to neutral after the droplet breaks off At block 135, the aptamers from the aptamer-target complexes are eluted from the beads and target, and amplified by enzymatic or chemical processes to optionally prepare for subsequent rounds of selection (repeat blocks 110-130, for example a SELEX protocol). The stringency of the elution conditions can be increased to identify the tightest-binding or highest affinity sequences. In some instances, once the aptamers are separated and amplified, the aptamers may be sequenced to identify the sequence and optionally a count for each aptamer. Optionally, the non-binding aptamers are eluted from the beads and are amplified by enzymatic or chemical processes. In some instances, once the non-binding aptamers are separated and amplified, the non-binding aptamers may be sequenced to identify the sequence and optionally a count for each non-binding aptamer. The count of non-binding aptamers may provide information on which aptamers have the weakest binding, which may supplement or validate the results of the aptamers found to bind. If aptamers are high in count for non-binding and low in count for binding, then aptamers may be determined and validated to have a weak binding affinity. If certain aptamers have significant counts for both binding and non-binding, the aptamers may be limited for some other reason (e.g., competition for binding sites among same type of aptamers).

At block 140, the sequence, the count, and an analysis performed based on the separation protocol (e.g., a binary classifier or a multiclass classifier) for each aptamer that has gone through the selection process of steps 110-130 are processed for application in downstream machine-learning processes. Each aptamer may include only the binding aptamers (those that formed the aptamer-target complexes), only the non-binding aptamers (those that did not form the aptamer-target complexes), or the combination thereof. In general, there are different types of binders (e.g., agonist, antagonist, allosteric, etc.) and those would be characteristics that the system may be configured to distinguish between the different types of binders during training, testing, and/or experimental analysis. In some instances, the sequence, count, and analysis for each aptamer is processed for use as training data, test data, or validation data in one or more machine-learning models. In other instances, the sequence, count, and analysis for each aptamer is processed for use as actual experimental data in one or more trained machine-learning models. In either instance, the sequence, count, and analysis for each aptamer may be processed to generate selection sequence data comprising a representation of the sequence of each aptamer, a count metric, an analysis metric, or any combination thereof. The representation of the sequence can include one-hot encoding of each nucleotide in the sequence that maintains information about the order of the nucleotides in the aptamer. The representation of the sequence can additionally or alternatively include other features concerning the sequence and/or aptamer, for example, post-translational modifications, binding sites, enzyme active sites, local secondary structure, kmers or characteristics identified for specific kmers, etc. The representation of the sequence can additionally or alternatively include a string of category identifiers, with each category representing a particular nucleotide. The count metric may include a count of the aptamer detected subsequent to an exposure to the target (e.g., during incubation and potentially in the presence of other aptamers). In some instances, the count metric includes a count of the aptamer detected subsequent to an exposure to the target in each round of selection. The analysis metric may include a binary classifier such as functionally inhibited the target, functionally did not inhibit the target, bound to the target, or did not bound to the target, a multiclass classifier such as a level of functional inhibition or a gradient scale for binding affinity.

At block 145, one or more machine-learning models are trained using the initial sequence data (from block 110), the selection sequence data (from block 135), or a combination thereof. The one or more machine-learning models may include a neural network, such as a feedforward neural network, recurrent neural network, convolutional neural network, and/or a deep neural network. The machine-learning models may be trained using training data, test data, and validation data based on sets of initial sequence data and selection sequence data to predict sequences for derived aptamers (e.g., aptamers not experimentally determined by a selection process but predicted based on aptamers experimentally determined by a selection process) and optional counts and/or analytics for the predicted sequences for derived aptamers. A loss function, such as an Mean Square Error (MSE), likelihood loss, or log loss (cross entropy loss), may be used to train each of the one or more machine-learning models. In some instances, a machine-learning model may be trained for predicting sequences for derived aptamers using the initial sequence data and/or the selection sequence data. Another machine-learning model may be trained for predicting binding counts for the predicted sequences for derived aptamers using the initial sequence data and/or the selection sequence data. Another machine-learning model may be trained for predicting analytics such as binding affinity for the predicted sequences for derived aptamers using the initial sequence data and/or the selection sequence data.

The trained machine-learning models can then be used to predict sequences for derived aptamers and optional counts and/or analytics for the predicted sequences for derived aptamers. For example, a subset of the aptamers experimentally determined by the in vitro selection process to satisfy the query (e.g., aptamers that have high binding affinity with a target or predicted counts due primarily to high binding affinity with a target) can be identified and separated from aptamers experimentally determined by the in vitro selection process to not satisfy the query. The subset of the aptamers experimentally determined by the in vitro selection process to satisfy the query can then be input into one or more machine learning models to identify in silico derived aptamer sequences (e.g., aptamer sequences that are derivatives of the experimentally selected aptamers) and optionally counts and analytics for the derived aptamer sequences. Optionally, the subset of the aptamers experimentally determined by the in vitro selection process to not satisfy the query can also be input into one or more machine learning models to assist in identifying in silico derived aptamer sequences (e.g., aptamer sequences that are derivatives of the experimentally selected aptamers) and optionally counts and analytics for the derived aptamer sequences.

The output can trigger in vitro experimental testing of some or all of the in silico derived aptamer sequences to experimentally measure analytics such as binding affinities with the target and/or binding affinities with one or more other targets. The experimental testing may be conditioned on input from a user. For example, a user device may present an interface in which the in silico derived aptamer sequences are identified along with input components configured to receive input to modify the in silico derived aptamer sequences (e.g., by removing or adding aptamers) and/or to generate an experiment-instruction communication to be sent to another device and/or other system. The experiment can include producing each of the in silico derived aptamer sequences. These aptamers can then be validated in the wet lab in either individual or bulk experiments. For example, the user can access a single aptamer (e.g. oligonucleotide). The single aptamer can be provided by an aptamer source, such as Twist Biosciences, Agilent, IDT, etc. The aptamer can be used to conduct biochemical assays (e.g. gel shift, surface plasma resonance, bio-layer interferometry, etc.). In some instances, multiple aptamers in a singular pool can be used to rerun the equivalent SELEX protocol (e.g., blocks 115-140) to identify enriched aptamers. Results can be assessed to determine whether the computational experiments are verified. In some instances, selections can be run in a digital format (i.e., ones that gave a functional output per sequence) to validate particular sequences. The validated sequences can be used to update the training set because the pair of sequence and affinity metric can be both normalized and calibrated.

Figure 1B:
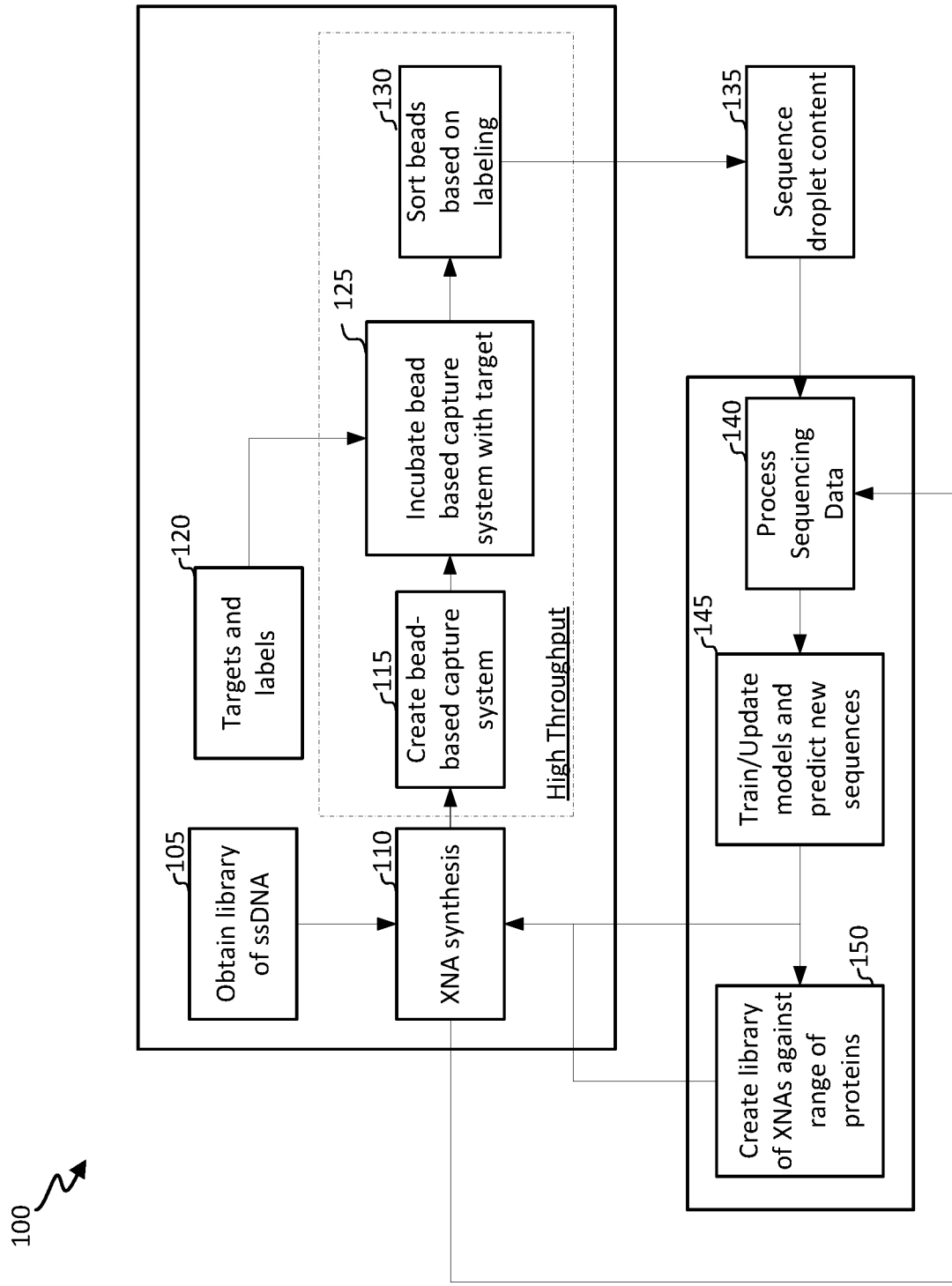

FIG. 1B shows a block diagram of an alternative aptamer development platform 100 for strategically identifying particular aptamers for in vitro experiments to assess queries such as binding affinities or product inhibition with respect to one or more particular targets. In various embodiments, the aptamer development platform 100 implements screening-based techniques for aptamer discovery where each aptamer candidate sequence in a library is assessed based on the query (e.g., binding affinity with one or more targets or functionally capable of inhibiting one or more targets) in a high-throughput manner, as described with respect to FIG. 1A. Additionally, the aptamer development platform 100 may implement machine learning based techniques for enhanced aptamer discovery where a library of predicted sequences for derived aptamers against a range of queries and/or targets is generated for subsequent processing (e.g., used as a base library of aptamer sequences in experimental testing (steps 110-140), instead of a random pool of oligonucleotides or aptamers, to answer a new query).

More specifically, at step 150, the output of the trained machine-learning models (sequences for derived aptamers and optional counts and/or analytics of the predicted sequences for derived aptamers) can trigger recording of some or all of the in silico derived aptamer sequences (e.g., positive and negative aptamer data such as predicted counts demonstrating increased binding affinity for a target or predicted counts demonstrating decreased binding affinity for a target) within a data structure (e.g., a database table). In some instances, the sequences for the derived aptamers are recorded in the data structure in association with additional information including the query, the one or more targets that are the focus of the query and basis for the genesis of the sequences for the derived aptamers, counts predicted for the sequences for the derived aptamers, analysis predicted for the sequences for the derived aptamers, or any combination thereof.

As should be understood, the aptamer development platform 100 described with respect to FIGS. 1A and 1B could be used for aptamer discovery where steps 110-140 are run in parallel to generate multiple monoclonal beads against multiple targets in association with one or more queries. Additionally or alternatively, the aptamer development platform 100 described with respect to FIGS. 1A and 1B could be used for aptamer discovery where steps 110-145 are run in parallel to generate multiple monoclonal beads against multiple targets in association with one or more queries and predict in parallel sequences for derived aptamers and optional counts and/or analytics for the predicted sequences for derived aptamers. The machine-learning models trained and used to make the predictions may be updated with results from the experiments and other machine-learning models using a distributed or collaborative learning approach such as federate learning which trains machine-learning models using decentralized data residing on end devices or systems. For example, a central or primary model may be updated or trained with results from all experiments being run and the results of the updating/training of the central or primary model may be propagated through to deployed secondary models (e.g., if information is obtained on cytokine a then the system may use that information to potential refine processes to identify for cytokine b). Aptamer sequences predicted to bind to a particular protein related to tumor subtypes using aptamer development platform 100 may form an aptamer family for use in embodiments described herein.

III. Modeling Techniques to Predict Sequences for Derived Aptamers

Figure 2:
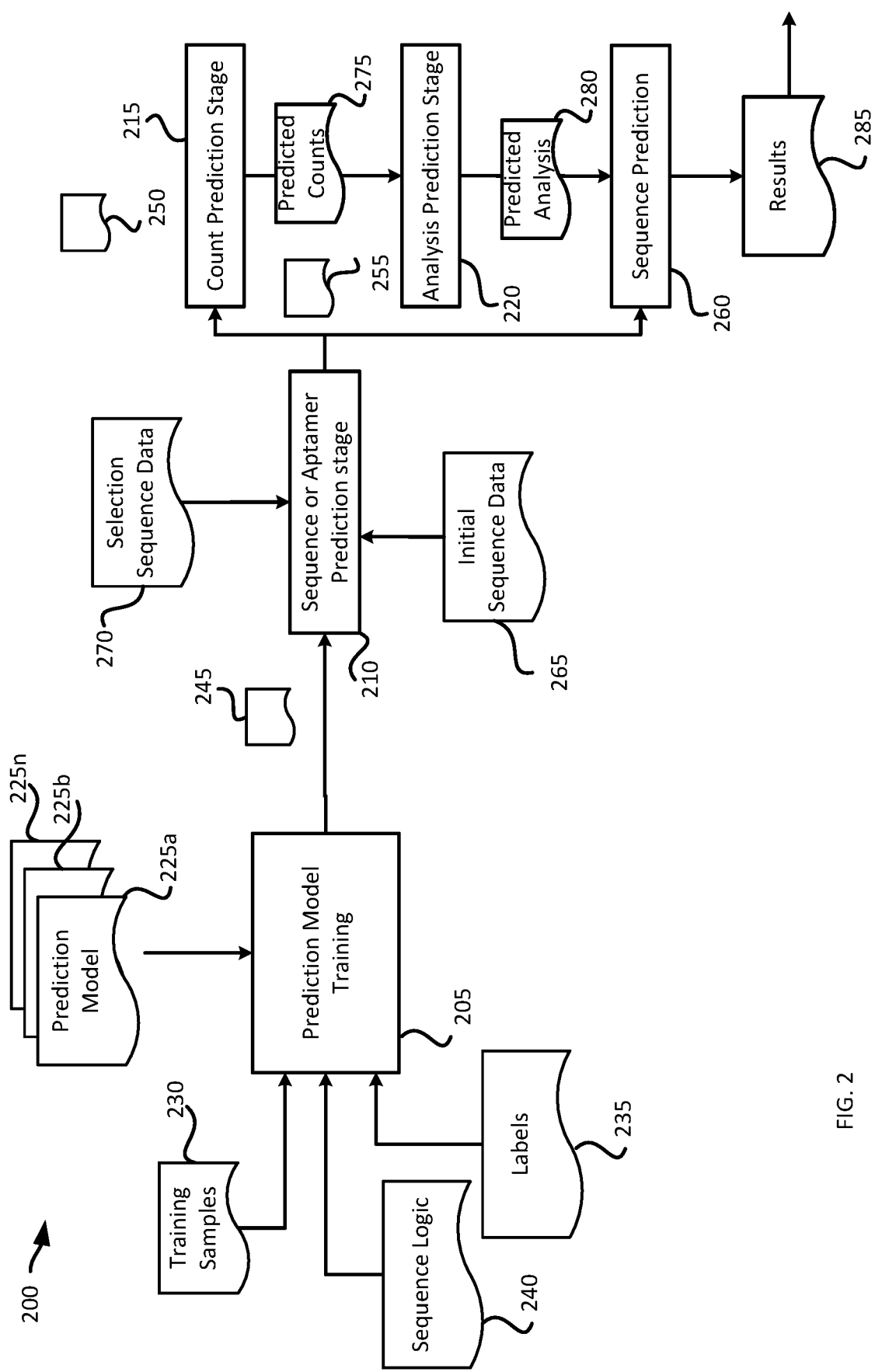
FIG. 2 shows a machine-learning modeling system for developing aptamers in accordance with various embodiments

FIG. 2 shows a block diagram illustrating embodiments of a machine-learning modeling system 200 for predicting sequences for derived aptamers (e.g., aptamers that answer a query posed by a user). As shown in FIG. 2, the predictions performed by the machine-learning modeling system 200 in this example include several stages: a prediction model training stage 205, a sequence or aptamer prediction stage 210, a count prediction stage 215, and an analysis prediction stage 220. The prediction model training stage 205 builds and trains one or more prediction models 225a-225n ('n' represents any natural number) to be used by the other stages (which may be referred to herein individually as a prediction model 225 or collectively as the prediction models 225). For example, the prediction models 225 can include a model for predicting sequences or aptamers not experimentally determined by a selection process but predicted based on aptamers experimentally determined by a selection process. The prediction models 225 can also include a model for predicting binding counts for the predicted sequences for derived aptamers. The prediction models 225 can also include a model for predicting analytics such as binding affinity for the predicted sequences for derived aptamers. Still other types of prediction models may be implemented in other examples according to this disclosure.

A prediction model 225 can be a machine-learning model, such as a neural network, a convolutional neural network ("CNN"), e.g. an inception neural network, a residual neural network ("Resnet") or NASNET provided by GOOGLE LLC from MOUNTAIN VIEW, CALIFORNIA, or a recurrent neural network, e.g., long short-term memory ("LSTM") models or gated recurrent units ("GRUs") models. A prediction model 225 can also be any other suitable machine-learning model trained to predict latent variables, sequence counts or aptamer sequences from experimentally determined aptamer sequences, such as a support vector machine, decision tree, a three-dimensional CNN ("3DCNN"), a dynamic time warping ("DTW") technique, a hidden Markov model ("HMM"), etc., or combinations of one or more of such techniques—e.g., CNN-HMM or MCNN (Multi-Scale Convolutional Neural Network). In various instances, at least one of the prediction models 225a-n includes structures related to a loss function prior to training. The machine-learning modeling system 200 may employ the same type of prediction model or different types of prediction models for aptamer sequence prediction, aptamer count prediction, and analysis prediction.

To train the various prediction models 225 in this example, training samples 230 for each prediction model 225 are obtained or generated. The training samples 230 for a specific prediction model 225 can include the initial sequence data and the selection sequence data as described with respect to FIG. 1 and optional labels 235 corresponding to the initial sequence data and the selection sequence data. For example, for a prediction model 225 to be utilized to predict derived aptamer sequences based on a given sequence, the input can be the aptamer sequence itself or features extracted from the selection sequence data associated with the aptamer sequence and optional labels 235 can include known derivative sequences. Similarly, for a prediction model 225 to be utilized to predict a count or binding affinity for an aptamer sequence, the input can include the sequence and count features extracted from the initial sequence data and/or the selection sequence data associated with the sequence, and the optional labels 235 can include features indicating parameters for the count or binding affinity or a vector indicating probabilities for the count or binding affinity of the selection sequence data.

In some instances, the training process includes iterative operations to find a set of parameters for the prediction model 225 that minimizes a loss function for the prediction models 225. Each iteration can involve finding a set of parameters for the prediction model 225 so that the value of the loss function using the set of parameters is smaller than the value of the loss function using another set of parameters in a previous iteration. The loss function can be constructed to measure the difference between the outputs predicted using the prediction models 225 and the optional labels 235 contained in the training samples 230. Once the set of parameters are identified, the prediction model 225 has been trained and can be tested, validated, and/or utilized for prediction as designed.

In addition to the training samples 230, other auxiliary information can also be employed to refine the training process of the prediction models 225. For example, sequence logic 240 can be incorporated into the prediction model training stage 205 to ensure that the sequences or aptamers, counts, and analysis predicted by a prediction model 225 do not violate the sequence logic 240. For example, binding affinity (the strength of the binding interaction between an aptamer and a target) is a characteristic that can drive aptamers to be present in greater numbers in a pool of aptamer-target complexes after a cycle of selection process. This relationship can be expressed in the sequence logic 240 such that as the binding affinity variable increases the predictive count increases (to represent this characteristic), as the binding affinity variable decreases the predictive count decreases. Moreover, an aptamer sequence generally has inherent logic among the different nucleotides. For example, GC content for an aptamer is typically not greater than 60%. This inherent logical relationship between GC content and aptamer sequences can be exploited to facilitate the aptamer sequence prediction.

According to some embodiments of the disclosure presented herein, the logical relationship between the binding affinity and count can be formulated as one or more constraints to the optimization problem for training the prediction models 225. A training loss function that penalizes the violation of the constraints can be built so that the training can take into account the binding affinity and count constraints. Alternatively, or additionally, structures, such as a directed graph, that describe the current features and the temporal dependencies of the prediction output can be used to adjust or refine the features and predictions of the prediction models 225. In an example implementation, features may be extracted from the initial sequence data and combined with features from the selection sequence data as indicated in the directed graph. Features generated in this way can inherently incorporate the temporal, and thus the logical, relationship between the initial library and subsequent pools of aptamer sequences after cycles of the selection process. Accordingly, the prediction models 225 trained using these features can capture the logical relationships between sequence characteristics, selection cycles, aptamer sequences, and nucleotides.

Although the training mechanisms described herein mainly focus on training a prediction model 225, these training mechanisms can also be utilized to fine tune existing prediction models 225 trained from other datasets. For example, in some cases, a prediction model 225 might have been pre-trained using pre-existing aptamer sequence libraries. In those cases, the prediction models 225 can be retrained using the training samples 230 containing initial sequence data, experimentally derived selection sequence data, and other auxiliary information as discussed herein.

The prediction model training stage 205 outputs trained prediction models 225 including the trained sequence prediction models 245, trained count prediction models 250, and trained analysis prediction models 255. The trained sequence prediction models 245 may be used in the sequence prediction stage 210 to generate sequence predictions 260 for a subset or all of the initial sequence data 265 and/or the selection sequence data 270 identified during the experimental selection process (e.g., steps 110-140 described with respect to FIGS. 1A and 1B). The trained count prediction models 250 may be used in the count prediction stage 215 to generate count predictions 275 for the predicted sequences based on the initial sequence data 265 and/or the selection sequence data 270 identified during the experimental selection process (e.g., steps 110-140 described with respect to FIGS. 1A and 1B). The trained analysis prediction models 255 may be used in the analysis prediction stage 220 to generate analysis predictions 280 (e.g., a binary classifier such as binds to target or does not bind to target) for the predicted sequences based on the initial sequence data 265 and/or the selection sequence data 270 identified during the experimental selection process (e.g., steps 110-140 described with respect to FIGS. 1A and 1B). In some instances, a results stage 285 may use the sequence predictions 260, count predictions 275, analysis predictions 280, or any combination thereof to provide results to a query posed by a user. For example, the results stage 285, in response to query for top ten aptamers that bind a given target, may provide the sequence predictions for ten aptamers with the highest count or binding affinity for the given target. The resulting aptamers at stage 285 may form an aptamer family for use in embodiments characterizing subtypes of tumor cells.

IV. Methods for Characterizing Subtypes of Tumor Cells

Figure 3:
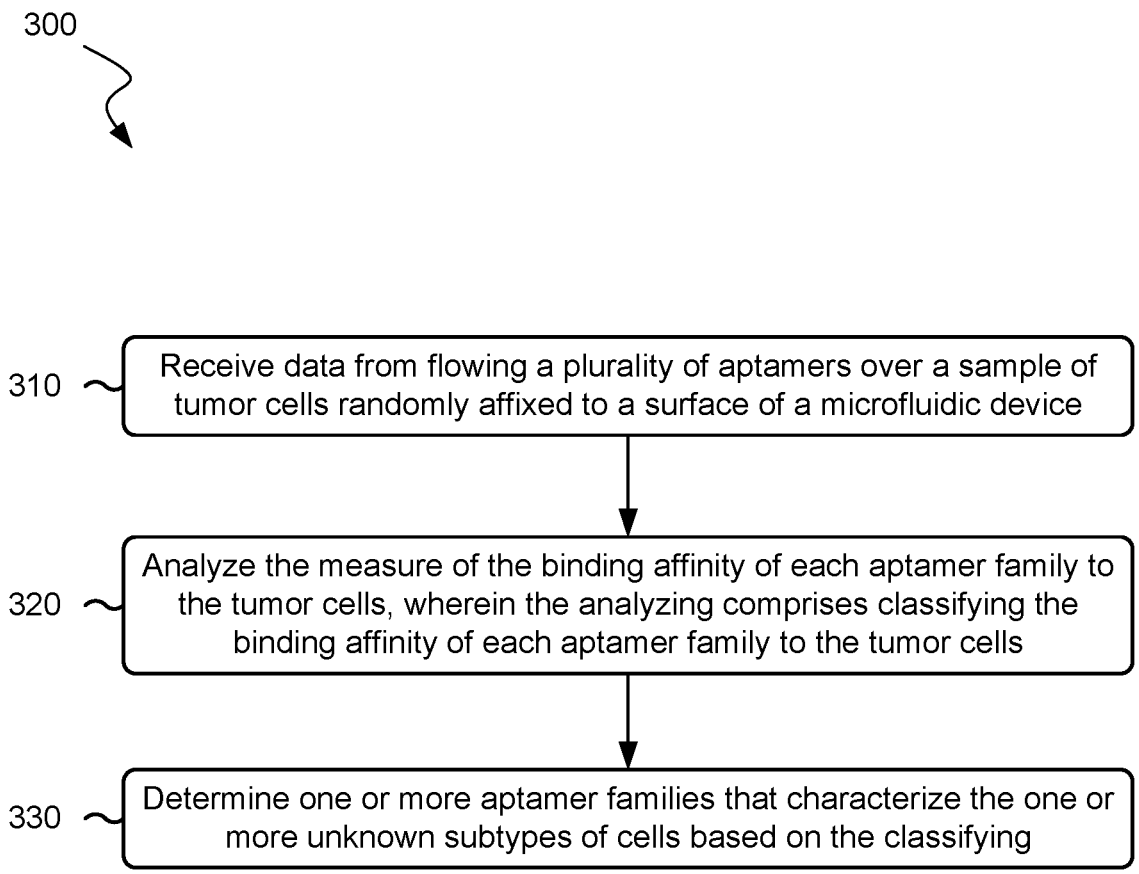
FIG. 3 is a flowchart of an example process 300 associated with cell analysis using aptamers and microfluidic systems according to embodiments of the present invention.

FIG. 3 is a flowchart of an example process 300 associated with cell analysis using aptamers and microfluidic systems. In some implementations, one or more process blocks of FIG. 3 may be performed by a system (e.g., system 400 of FIG. 4). In some implementations, one or more process blocks of FIG. 3 may be performed by another device or a group of devices separate from or including the system. Additionally, or alternatively, one or more process blocks of FIG. 3 may be performed by one or more components of computing device 500, such as processor 505, memory 510, bus 515, user input device(s) 530, display 535, and/or communications interface 540. Process 300 may include additional implementations, such as any single implementation or any combination of implementations described below and/or in connection with one or more other processes described elsewhere herein.

At block 310, process 300 includes receiving data from flowing a plurality of aptamers over a sample of tumor cells randomly affixed to a surface of a microfluidic device. For example, the system may receive data from flowing a plurality of aptamers over a sample of tumor cells randomly affixed to a surface of a microfluidic device. The sample may be a liquid biopsy of the tumor cells obtained from a fluid of the subject. In some instances, the sample may be a tumor biopsy. In some implementations, process 300 may include introducing the plurality of aptamers to the microfluidic device and flowing the plurality of aptamers over the tumor cells randomly affixed to the surface of the microfluidic device. The plurality of aptamers may include 100,000 to 1 million, 1 to 5 million, 5 to 10 million, or more than 10 million aptamers. The random arrangement of tumor cells means that the tumor cells are not arranged by tumor subtype, mass, receptor type, or other characteristic on the surface of the microfluidic device.

The tumor cells may be from a tumor resulting from any type of cancer. Types of cancer may include bladder cancer, breast cancer, colon and rectal cancer, endometrial cancer, kidney cancer, leukemia (e.g., acute myeloid leukemia), liver cancer, lung cancer, melanoma, non-Hodgkin lymphoma, pancreatic cancer, prostate cancer, or thyroid cancer. The tumor may be benign or malignant. In some embodiments, the cancer may be an orphan disease (e.g., a disease or condition that affects fewer than 200,000 people in the United States or fewer than about 1 in 1,500 people).

The fluid of the subject may be a biological fluid. The subject may be a human subject or other mammalian subject. A biological fluid may be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g. thyroid, breast), etc. Stool samples can also be used. In some embodiments, process 300 may include obtaining the biological fluid from the human subject. In some embodiments, the biological fluid may be enriched for the tumor cells.

The tumor cells may include one or more unknown tumor subtypes of cells. Each tumor subtype of cell may include a common genetic marker or a common receptor that is different from those of other tumor subtypes. The common receptor may be bound by aptamers. Unknown tumor subtypes may refer to the presence of the subtype in the tumor cells not being known or being as-yet unidentified for the specific tumor sample. In some embodiments, an unknown tumor subtype may refer to the tumor subtype not being previously characterized.

The plurality of aptamers may include a plurality of aptamer families. Each aptamer of an aptamer family may include a common sequence that is not present in other aptamer families. The common sequence may be at an end of an aptamer or may be in the middle of an aptamer. The common sequence may include 3, 4, 5, 6, 7, 8, 9, 10, 10 to 15, 15 to 20, or 20 or more nucleotides. Each aptamer family may include from 10 to 100, 100 to 1,000, 1,000 to 2,000, 2,000 to 5,000, or more than 5,000 unique aptamer sequences. Each unique aptamer sequence may include 10 to 100, 100 to 1,000, 1,000 to 5,000, or more than 5,000 replicates. In some embodiments, each aptamer of an aptamer family may bind to a common receptor or may have a minimum binding affinity for a common receptor. The common receptor that is bound by one aptamer family may not be bound by other aptamer families. Each aptamer family of the plurality of aptamer families may be determined by a prediction model to bind to at least one possible subtype of the tumor cells. Possible tumor subtypes may be tumor subtypes that are known generally for tumor cells but not yet identified for the particular tumor sample. The plurality of aptamer families may be at least 2, 3, 4, 5, 6, 7, 8, 9, 10, 10 to 15, 15 to 20, 20 to 50, or 50 or more aptamer families. The plurality of aptamer families may include more aptamer families than a number of tumor subtypes of the one or more unknown subtypes of the tumor cells in order to ensure identification of as many unknown tumor subtypes as possible. The aptamer family may be a library of aptamers, which may be developed using the platforms described with FIGS. 1A and 1B and predicted using techniques described with FIG. 2.

The data may include a measure of binding affinity of each aptamer family to the tumor cells. In some implementations, the measure of the binding affinity of each aptamer family may be an elution time. A faster elution time may indicate a weaker binding affinity. Different aptamer families may be flowed over the tumor sample starting at the same time. An aptamer family with a higher binding affinity will bind and take longer to release relative to an aptamer family with a lower binding affinity. In other implementations, the measure of the binding affinity each aptamer family may be an amount of aptamers that bind to the tumor cells. In some embodiments, the distance that an aptamer family elutes in a certain amount of time may be used to determine a binding affinity. A greater distance traveled may indicate a weaker binding affinity. Measures of binding affinities may be a statistical value (e.g., mean, median, mode, percentile). Elution time or distance may be determined using aptamers tagged with a label. For example, aptamers may be tagged with a fluorescent label, and measurement of elution time or distance may use detection of the fluorescence or quantification of an intensity.

A greater number of aptamers that bind may indicate a stronger binding affinity. The number of aptamers may be determined through different techniques. In some implementations, each aptamer of the plurality of aptamers may be tagged with a fluorescent label, and the measure of the binding affinity may be a fluorescent intensity associated with the binding each aptamer family to the tumor cells. Each aptamer family may be tagged with a unique label to distinguish from other aptamer families. Measures of binding affinities may be monitored in real-time. For example, the fluorescent intensity may be measured as different aptamer families are flowed over the tumor cells. In some embodiments, the microfluidic flow cell may be washed of unbound aptamers. The bound aptamers may then be released from the tumor cells through heating the microfluidic flow cell. These previously bound aptamers may then be sequenced to determine the aptamer families and amounts of aptamers that bind to the tumor subtypes. In some embodiments, the previously bound aptamers may be labeled with fluorescent tags or other tags, and the tags may be quantified by suitable techniques (e.g., FACS).

At block 320, process 300 includes analyzing the measure of the binding affinity of each aptamer family to the tumor cells. The analyzing may include classifying the binding affinity of each aptamer family to the tumor cells. Classifying the binding affinity of each aptamer family may include ranking the binding affinity of aptamer families. The ranking may be an ordinal ranking. The aptamer families may be ranked from highest binding affinity to weakest binding affinity or in the opposite order.

In some implementations, classifying the binding affinity may include comparing the binding affinity against one or more thresholds. A binding affinity above a threshold may be in one classification indicating a high binding affinity, while a binding affinity below the threshold may be in a second classification indicating a low binding affinity. An additional threshold may be used to create a classification for a medium binding affinity. More thresholds may be used to create additional classifications of binding activity. The thresholds may be based on reference aptamers. For example, an aptamer may be known to bind with a certain subtype of tumor cell. The binding affinity of that interaction may be used as a threshold. Another aptamer may be known to not bind well with a certain subtype of tumor cell. The binding affinity of that interaction may be used as another threshold. Several reference aptamers may be used. Thresholds may be determined as indicating a value of a binding affinity statistically different from binding affinities generated from a certain type of reference aptamer and tumor subtype (e.g., non-binding or binding pairs).

At block 330, process 300 includes determining one or more aptamer families that characterize the one or more unknown tumor subtypes of cells based on the classifying. The one or more aptamer families that characterize the one or more unknown tumor subtypes may be the one or more aptamer families that best represent the one or more unknown tumor subtypes. The one or more aptamer families may serve as a type of fingerprint for the one or more unknown tumor subtypes. For example, the one or more aptamer families may not be determined to characterize tumor subtypes of cells that include more or fewer tumor subtypes of cells than the one or more unknown tumor subtypes. A classification associated with a higher binding affinity may result in the aptamer family being determined as characterizing the one or more unknown tumor subtypes of cells. In some embodiments, a certain number of aptamer families with the highest ranking binding affinities may be determined to characterize the one or more unknown tumor subtypes of cells. For example, the top 2, 3, 4, or 5 to 10 ranked aptamer families may be considered to characterize the one or more unknown tumor subtypes. In some examples, the top 10%, 15%, 20%, 25%, 30%, 40%, or 50% of aptamer families based on binding affinity may be considered to characterize the one or more unknown tumor subtypes. In some embodiments, the identity of the one or more unknown tumor subtypes of cells may not be determined. Determining the one or more aptamer families that characterize the one or more tumor subtypes of cells may be sufficient. The characterization of the tumor subtypes using the one or more aptamer families may indirectly provide information on the tumor subtypes without definitively identifying the tumor subtypes. Characterizing the tumor subtypes with aptamer families may also provide information on the types of binding sites (e.g., receptors) present on tumor cells, which may aid in design of therapeutics.

In some implementations, process 300 may include treating a subject having the tumor cells using the one or more aptamer families that characterize the one or more tumor subtypes of cells. The aptamer families may be delivered into the subject. The aptamer families may be linked to a therapeutic to deliver the therapeutic to the associated tumor subtypes of cells. The therapeutic may be known to attack the associated tumor subtypes. In some implementations, the aptamer families may be linked to a cytotoxic agent. The treatment may include aptamer families introduced in a concentration proportional to their binding affinities. An aptamer family with the highest binding affinity may have the highest concentration in the treatment. Different aptamer families may be introduced sequentially, including in the order of their binding affinities. The aptamer family with the highest binding affinity may be used to treat the subject first. Then the aptamer family with the second highest binding affinity may then be used to treat the subject. The time between the different aptamer family treatments may be an hour, a day, a week, or a month. In some embodiments, after treatment with the aptamer family with the highest binding affinity, the sample may be re-analyzed to re-characterize the one or more unknown tumor subtypes of the cells. A different aptamer family may be then be used to treat the subject based on the re-characterization.

In embodiments, process 300 may include identifying the one or more unknown tumor subtypes of cells of the tumor cells to obtain one or more identified tumor subtypes based on (i) the determining of the one or more aptamer families that characterize the one or more tumor subtypes of cells based on the classifying, and (ii) the at least one possible tumor subtype of the tumor cells that each aptamer family is determined to bind to by the prediction model. For example, the prediction model may determine that a first aptamer family binds to a first tumor subtype of cells, that a second aptamer family binds to a second tumor subtype of cells, etc. The first aptamer family and the second aptamer family may be determined to characterize the one or more tumor subtypes of cells based on the classifying. As a result, the one or more unknown tumor subtypes of cells may be identified as including the first tumor subtype of cells and the second tumor subtype of cells. In some embodiments, the relative population of the tumor subtypes may be determined from the aptamer families that characterize the one or more tumor subtypes. A greater amount of bound aptamer may correlate with a greater amount of the associated tumor subtype. The ranking of the tumor subtypes based on amount may correlate with the ranked amounts of aptamer families bound to the tumor subtypes.

In some implementations, process 300 includes determining a treatment protocol for the subject having the tumor cells based on the one or more identified tumor subtypes. Process 300 may include treating the subject based on the treatment protocol. The treatment protocol may include any treatment with aptamer families described herein.

In implementations, process 300 may include ascertaining a level of cancer based on the one or more identified tumor subtypes. A level of cancer may refer to whether cancer exists, a stage of cancer, a size of tumor, whether there is metastasis, the total tumor burden of the body, and/or other measure of a severity of cancer. The level could be zero. The level of cancer also includes premalignant or precancerous conditions (states) associated with mutations or a number of mutations. Ascertaining the level of cancer may include analyzing clinical information (e.g., symptoms, genetic predisposition, family history, imaging scans) in addition to using the one or more identified tumor subtypes.

Samples from reference subjects having known levels of cancer may be analyzed for tumor subtypes. The sample may be a tumor biopsy, a liquid biopsy, or any biopsy described herein. Certain tumor subtype(s), combinations of tumor subtypes, and/or amounts of tumor subtype(s) may be associated with a certain level of cancer. A calibration table may be developed to correlate existence of or amounts of tumor subtypes with levels of cancer. The one or more identified tumor subtypes may be compared to the calibration table and a level of cancer may be determined. In some embodiments, aptamer families may be directly associated with levels of cancer by having a calibration table that associates aptamer families with levels of cancer, without needing to identify the tumor subtypes of cells.

In some embodiments, the level of cancer may be a score. The score may be calculated from the identities of the tumor subtypes and the relative amounts of the tumor subtypes identified in the tumor cells. Certain tumor subtypes may be associated with more severe levels of cancer. The severity score due to one tumor subtype may be related to a product of the amount of the tumor subtype present and a number representing the severity of the particular tumor subtype. The level of cancer may be the summation of severity scores for the different tumor subtypes. An analogous severity score may be calculated from the aptamer families that characterize the tumor cells.

The level of cancer may be monitored over time for a subject. Changes in the subtypes of tumor cells may indicate that cancer may be progressing or that treatment may be effective. For example, a tumor subtype may be known to be more malignant than another tumor subtype. The reduction in the number of that tumor subtype may indicate that the level of cancer is becoming less severe, which may be the result of a treatment. The treatment may be maintained or adjusted based on results from monitoring the level of cancer.

In implementations, aptamer families may be tested in a microfluidic device two at a time and rankings of binding affinities may be based on the results of these pairwise tests. For example, the data may include results from flowing a first aptamer family and a second aptamer family concurrently over the tumor cells. The first aptamer family may be determined by the prediction model to bind to a first possible tumor subtype. The second aptamer family may be determined by the prediction model to bind to a second possible tumor subtype. The data may include results from flowing the first aptamer family and a third aptamer family concurrently over the tumor cells. The third aptamer family may be determined by the prediction model to bind to a third possible tumor subtype. The second aptamer family and the third aptamer family may not be flowed concurrently over the tumor cells. The method may further include determining that the measure of the binding affinity for the first aptamer family is greater than the measure of the binding affinity for the second aptamer family. The method may also include determining that the measure of the binding affinity for the third aptamer family is greater than the measure of the binding affinity for the first aptamer family. In addition, the method may include determining that the third possible tumor subtype has a higher population in the tumor cells than the first tumor subtype and that the first possible tumor subtype has a higher population than the second possible tumor subtype. In some embodiments, more than two aptamer families may be tested in a microfluidic device at a time. Fractional factorial design or other techniques may be used to design experiments and analyze results.

The prediction model for determining binding to at least one possible subtype of the tumor cells may be a machine learning model, including a model described with FIG. 2 or in U.S. application Ser. No. 17/126,842, filed Dec. 18, 2020, the entire contents of which are incorporated herein by reference for all purposes. Each aptamer family of the plurality of aptamer families may be determined by synthesizing an aptamer library from one or more single stranded DNA or RNA (ssDNA or ssRNA) libraries. The aptamer family may further be determined by partitioning a plurality of aptamers within the aptamer library into monoclonal compartments that combined establish a compartment-based capture system. Each monoclonal compartment may include a unique aptamer from the plurality of aptamers. The determination of the aptamer family may also include capturing one or more targets. The capturing may include the one or more targets binding to the unique aptamer within one or more monoclonal compartments. The determination of the aptamer family may further include separating the one or more monoclonal compartments of the compartment-based capture system that include the one or more targets bound to the unique aptamer from a remainder of monoclonal compartments of the compartment-based capture system that do not include the one or more targets bound to a unique aptamer. The unique aptamer from each of the one or more monoclonal compartments may be sequenced. Sequencing may include generating sequencing data and analysis data for the unique aptamer from each of the one or more monoclonal compartments. The determination of the aptamer family may include generating, by the prediction model, one or more aptamer sequences derived from the sequencing data and the analysis data for at least some of the unique aptamers from the one or more monoclonal compartments. An aptamer family of the plurality of aptamer families may include the one or more aptamer sequences.

In some embodiments, one or more subtypes of tumor cells may have some receptors that are bound by aptamers but these receptors may be known to not be good sites for delivering a therapeutic. In these instances, an aptamer family that is predicted to bind or known to bind to these receptors may be flowed over the tumor cells. As a result, the aptamer family may bind these ineffective receptors and mask the receptors before other aptamer families are flowed over the tumor cells.

Although FIG. 3 shows example blocks of process 300, in some implementations, process 300 may include additional blocks, fewer blocks, different blocks, or differently arranged blocks than those depicted in FIG. 3. Additionally, or alternatively, two or more of the blocks of process 300 may be performed in parallel. Process 300 may be instructions stored in a non-transitory computer readable storage medium. The non-transitory computer readable storage medium may be part of a system or a computer-program product.

V. Example Systems

Figure 4:
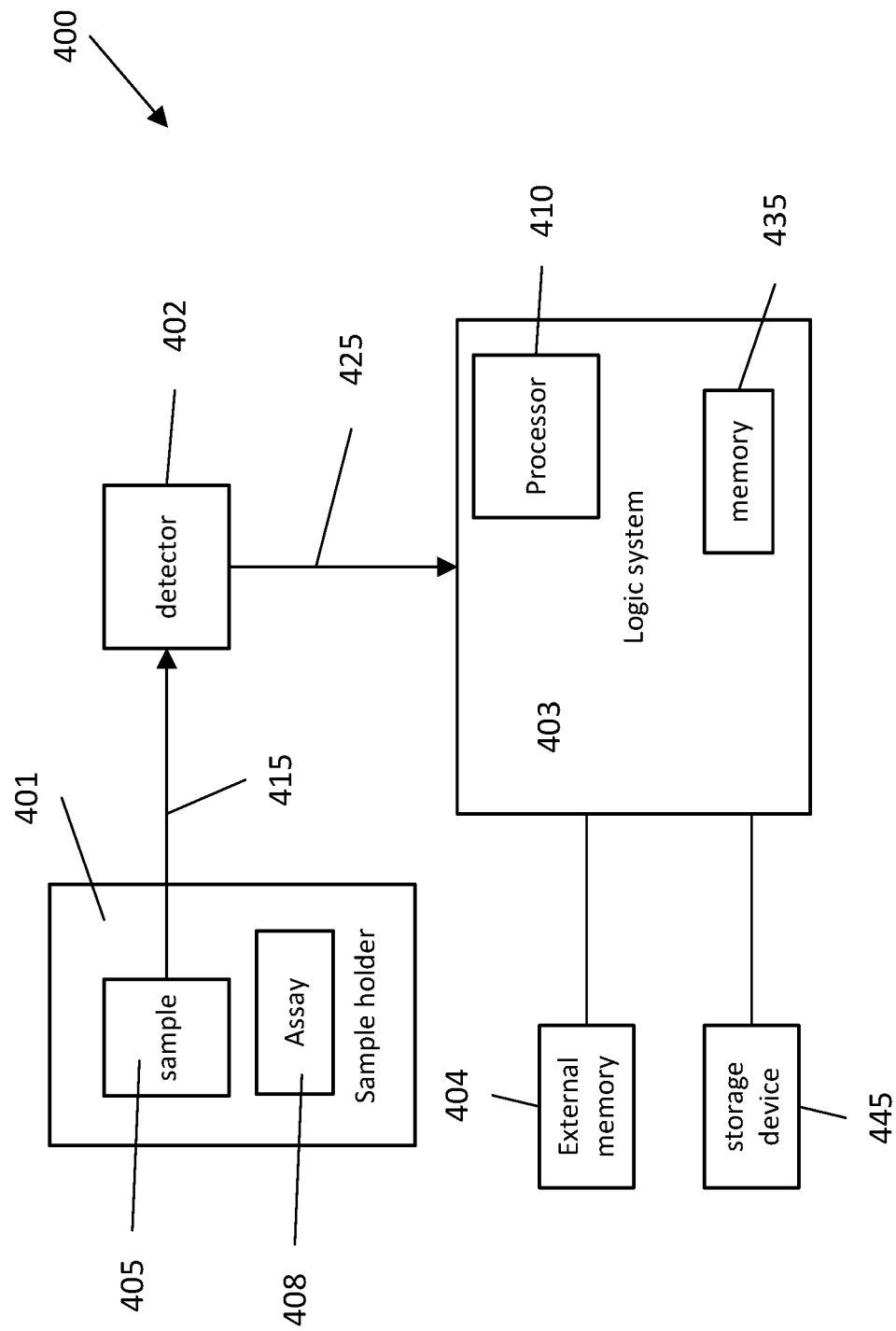
FIG. 4 illustrates a measurement system according to embodiments of the present invention.

FIG. 4 illustrates a measurement system 400 according to an embodiment of the present invention. The system as shown includes a sample 405, such as DNA molecules within a sample holder 401, where sample 405 can be contacted with an assay 408 to provide a signal of a physical characteristic 415. An example of a sample holder can be a microfluidic flow cell that includes probes and/or primers of an assay or a tube through which a droplet moves (with the droplet including the assay). The droplet may include the aptamer families. Physical characteristic 415 (e.g., a fluorescence intensity, a voltage, or a current), from the sample is detected by detector 420. Detector 402 can take a measurement at intervals (e.g., periodic intervals) to obtain data points that make up a data signal. In one embodiment, an analog-to-digital converter converts an analog signal from the detector into digital form at a plurality of times. Sample holder 401 and detector 402 can form an assay device, e.g., a sequencing device that performs sequencing according to embodiments described herein or a fluorescence measurement device that measures fluorescent intensities associated with bound aptamers. A data signal 425 is sent from detector 402 to logic system 403. Data signal 425 may be stored in a local memory 435, an external memory 404, or a storage device 445.

Logic system 403 may be, or may include, a computer system, ASIC, microprocessor, etc. It may also include or be coupled with a display (e.g., monitor, LED display, etc.) and a user input device (e.g., mouse, keyboard, buttons, etc.). Logic system 403 and the other components may be part of a stand-alone or network connected computer system, or they may be directly attached to or incorporated in a device (e.g., a microfluidic flow cell analysis device) that includes detector 402 and/or sample holder 401. Logic system 403 may also include software that executes in a processor 410. Logic system 403 may include a computer readable medium storing instructions for controlling system 400 to perform any of the methods described herein. For example, logic system 403 can provide commands to a system that includes sample holder 401 such that sequencing or other physical operations are performed. Such physical operations can be performed in a particular order, e.g., with reagents being added and removed in a particular order. Such physical operations may be performed by a robotics system, e.g., including a robotic arm, as may be used to obtain a sample and perform an assay.

A microfluidic flow cell may be any device suitable for studying binding affinity between aptamers and tumor cells. The microfluidic flow cell may include a substrate. The volume of liquid involved in a microfluidic flow cell may be less than 1 mL, less than 1 μL, less than 1 nL, less than 1 pL, or between any two of these stated volumes. The microfluidic flow cell may include one portion where the tumor cells are affixed. A sample of aptamers may be introduced to an inlet. The inlet may lead to a channel or a series of channels, which lead to the area where the tumor cells are affixed. Downstream of the tumor cells may be a second channel or a second plurality of channels leading to an outlet. Analysis (e.g., detection or measurement) may occur at the outlet.

Figure 5:
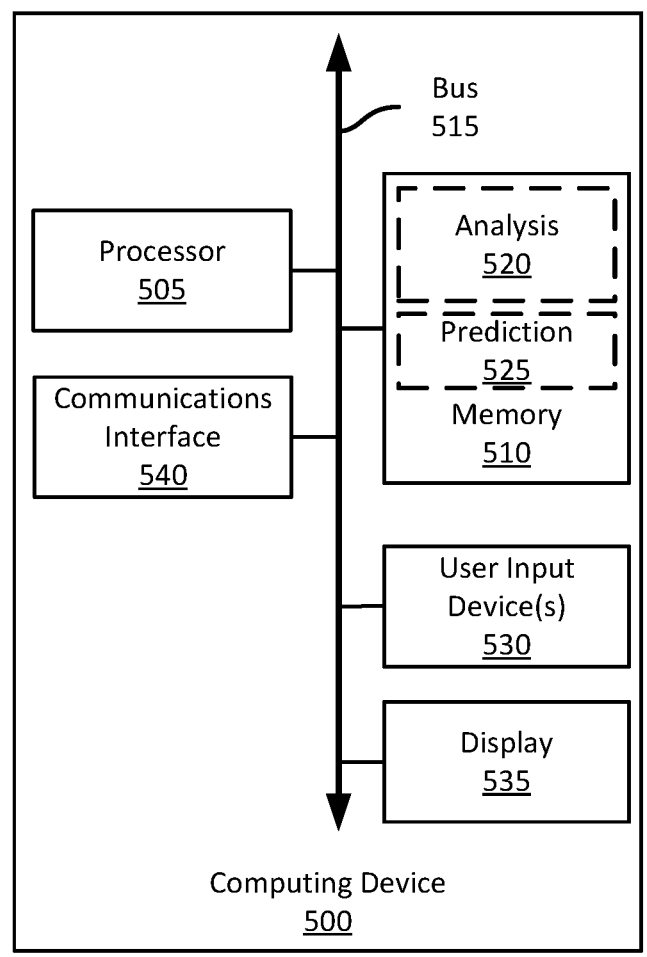
FIG. 5 shows an exemplary computing device in accordance with various embodiments.

FIG. 5 illustrates an example computing device 500 suitable for use with systems and methods for developing aptamers or providing results to a query according to this disclosure. Any of the computer systems mentioned herein may utilize any suitable number of subsytems, including those shown in FIG. 5. The example computing device 500 includes a processor 505 which is in communication with the memory 510 and other components of the computing device 500 using one or more communications buses 515. The processor 505 is configured to execute processor-executable instructions stored in the memory 510 to perform one or more methods for determining one or more aptamer families that characterize the one or more unknown tumor subtypes of cells, such as part or all of the example process 300 described above. In this example, the memory 510 stores processor-executable instructions that provide sequence data analysis 520 and aptamer sequence prediction 525, as discussed above with respect to FIGS. 1A, 1B, 2, and 3. Processor 505 may be processor 410. Memory 510 may be may be memory 435.

The computing device 500, in this example, also includes one or more user input devices 530, such as a keyboard, mouse, touchscreen, microphone, etc., to accept user input. The computing device 500 also includes a display 535 to provide visual output to a user such as a user interface. The computing device 500 also includes a communications interface 540. In some examples, the communications interface 540 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

VI. Additional Considerations

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" or "computer-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the particle" includes reference to one or more particles and equivalents thereof known to those skilled in the art, and so forth. The invention has now been described in detail for the purposes of clarity and understanding. However, it will be appreciated that certain changes and modifications may be practice within the scope of the appended claims.

All publications, patents, and patent applications cited herein are hereby incorporated by reference in their entirety for all purposes. None is admitted to be prior art.

What is claimed is:

1. A method comprising:
   assaying a sample of tumor cells using a microfluidic device, wherein the assaying comprises:
   randomly affixing the tumor cells to a surface of the microfluidic device; and
   flowing a plurality of aptamers over the tumor cells to allow the aptamers to interact and bind to the tumor cells,
   wherein:
   the tumor cells comprise one or more unknown subtypes of the tumor cells,
   the plurality of aptamers comprises a plurality of aptamer families, and
   each aptamer family of the plurality of aptamer families is determined by a prediction model to bind to at least one possible subtype of the tumor cells;
   obtaining data from assaying the sample of tumor cells, wherein
   the data comprises a measure of binding affinity of each aptamer family to the tumor cells;
   analyzing the measure of the binding affinity of each aptamer family to the tumor cells, wherein the analyzing comprises classifying the binding affinity of each aptamer family to the tumor cells; and
   determining one or more aptamer families that characterize the one or more unknown subtypes of the tumor cells based on the classifying.

2. The method of claim 1, wherein the measure of the binding affinity of each aptamer family is an elution time.

3. The method of claim 1, wherein the measure of the binding affinity each aptamer family is an amount of aptamers that bind to the tumor cells.

4. The method of claim 1, further comprising identifying the one or more unknown subtypes of the tumor cells to obtain one or more identified subtypes based on: (i) the determining of the one or more aptamer families that characterize the one or more subtypes of the tumor cells based on the classifying, and (ii) the at least one possible subtype of the tumor cells that each aptamer family is determined to bind to by the prediction model.

5. The method of claim 4, further comprising determining a treatment protocol for a subject having the tumor cells based on the one or more identified subtypes.

6. The method of claim 5, further comprising treating the subject based on the treatment protocol.

7. The method of claim 6, wherein the sample is a liquid biopsy of the tumor cells obtained from a fluid of the subject.

8. The method of claim 4, further comprising ascertaining a level of cancer based on the one or more identified subtypes.

9. The method of claim 1, further comprising treating a subject having the tumor cells using the one or more aptamer families that characterize the one or more subtypes of the tumor cells.

10. The method of claim 1, wherein the plurality of aptamer families is at least 3 aptamer families.

11. The method of claim 1, wherein the plurality of aptamer families comprises more aptamer families than a number of subtypes of the one or more unknown subtypes of the tumor cells.

12. The method of claim 1, wherein:
   the data comprises results from flowing a first aptamer family and a second aptamer family concurrently over the tumor cells,
   the first aptamer family is determined by the prediction model to bind to a first possible subtype,
   the second aptamer family is determined by the prediction model to bind to a second possible subtype, the data comprises results from flowing the first aptamer family and a third aptamer family concurrently over the tumor cells, the third aptamer family is determined by the prediction model to bind to a third possible subtype, the second aptamer family and the third aptamer family are not flowed concurrently over the tumor cells, the method further comprising:
  determining that the measure of the binding affinity for the first aptamer family is greater than the measure of the binding affinity for the second aptamer family,
  determining that the measure of the binding affinity for the third aptamer family is greater than the measure of the binding affinity for the first aptamer family,
  determining that the third possible subtype has a higher population in the tumor cells than the first subtype, and that the first possible subtype has a higher population than the second possible subtype.

13. A system comprising:
  a microfluidic device configured to perform an assay on a sample of tumor cells, wherein the microfluidic device comprises:
    a surface comprising randomly affixed tumor cells comprising one or more unknown subtypes of the tumor cells,
    a channel configured to deliver the sample to the surface and flow a plurality of aptamers over the tumor cells to allow the aptamers to interact and bind to the tumor cells, wherein the plurality of aptamers comprises a plurality of aptamer families, and each aptamer family of the plurality of aptamer families is determined by a prediction model to bind to at least one possible subtype of the tumor cells, and
    a detector configured to obtain data points that make up a data signal associated with a measure of binding affinity of each of the plurality of aptamer families to the tumor cells;
  one or more data processors; and
  a non-transitory computer readable storage medium containing instructions that, when executed on the one or more data processors, cause the one or more data processors to perform actions including:
    obtaining the data signal from the microfluidic device;
    analyzing the measure of the binding affinity of each aptamer family to the tumor cells, wherein the analyzing comprises classifying the binding affinity of each aptamer family to the tumor cells; and
    determining one or more aptamer families that characterize the one or more unknown subtypes of the tumor cells based on the classifying.

14. The system of claim 13, wherein the actions further include identifying the one or more unknown subtypes of the tumor cells to obtain one or more identified subtypes based on: (i) the determining of the one or more aptamer families that characterize the one or more subtypes of the tumor cells based on the classifying, and (ii) the at least one possible subtype of the tumor cells that each aptamer family is determined to bind to by the prediction model.

15. The system of claim 14, wherein the actions further include determining a treatment protocol for a subject having the tumor cells based on the identity of the one or more unknown subtypes of the tumor cells.

16. The system of claim 14, wherein the actions further include ascertaining a level of cancer based on the identity of the one or more unknown subtypes of the tumor cells.

17. A computer-program product tangibly embodied in a non-transitory machine-readable storage medium, including instructions configured to cause one or more data processors to perform actions including:
  obtaining a data signal from a microfluidic device configured to perform an assay on a sample of tumor cells, wherein the data signal is obtained by:
    flowing a plurality of aptamers over the tumor cells randomly affixed to a surface of the microfluid device, which allows the aptamers to interact and bind to the tumor cells, and
    obtaining data points that make up the data signal associated with a measure of binding affinity of each aptamer family of a plurality of aptamer families to the tumor cells, wherein the plurality of aptamers comprises the plurality of aptamer families, and each aptamer family of the plurality of aptamer families is determined by a prediction model to bind to at least one possible subtype of the tumor cells;
  analyzing the measure of the binding affinity of each aptamer family to the tumor cells, wherein the analyzing comprises classifying the binding affinity of each aptamer family to the tumor cells; and
  determining one or more aptamer families that characterize the one or more unknown subtypes of the tumor cells based on the classifying.

18. The computer-program product of claim 17, wherein the actions further include identifying the one or more unknown subtypes of the tumor cells to obtain one or more identified subtypes based on: (i) the determining of the one or more aptamer families that characterize the one or more subtypes of the tumor cells based on the classifying, and (ii) the at least one possible subtype of the tumor cells that each aptamer family is determined to bind to by the prediction model.

19. The computer-program product of claim 18, wherein the actions further include determining a treatment protocol for a subject having the tumor cells based on the one or more identified subtypes.

20. The computer-program product of claim 18, wherein the actions further include ascertaining a level of cancer based on the one or more identified subtypes.

* * * * *